US008214951B1

(12) United States Patent
Batta

(10) Patent No.: US 8,214,951 B1
(45) Date of Patent: Jul. 10, 2012

(54) SOFT SURGICAL ARM SUPPORT

(76) Inventor: Alex G. Batta, Riverside, CA (US)

(*) Notice: Subject to any disclaimer, the term of this patent is extended or adjusted under 35 U.S.C. 154(b) by 0 days.

(21) Appl. No.: 12/686,248

(22) Filed: Jan. 12, 2010

Related U.S. Application Data

(60) Provisional application No. 61/221,492, filed on Jun. 29, 2009.

(51) Int. Cl.
A47C 17/86 (2006.01)
(52) U.S. Cl. ............ 5/647; 5/646; 5/494; 128/878; 128/869
(58) Field of Classification Search ............ 5/646, 647, 5/494; 128/878, 869
See application file for complete search history.

(56) References Cited

U.S. PATENT DOCUMENTS

| 826,648 | A | | 7/1906 | Challenger | |
|---|---|---|---|---|---|
| 1,183,225 | A | | 5/1916 | Overmeyer | |
| 1,219,453 | A | * | 3/1917 | Hansen | 128/878 |
| 2,245,293 | A | | 6/1941 | Ogburn | |
| 2,256,642 | A | * | 9/1941 | Gaut et al. | 428/464 |
| 2,679,842 | A | * | 6/1954 | Brill | 128/878 |
| 2,848,993 | A | | 8/1958 | Terrell | |
| 2,995,407 | A | | 8/1961 | Izzi | |
| 3,010,452 | A | * | 11/1961 | Smith | 128/881 |
| 3,315,671 | A | | 4/1967 | Creelman | |
| 3,474,781 | A | | 10/1969 | Gaylord, Jr. | |
| 3,861,666 | A | | 1/1975 | Nishiyama et al. | |
| 3,920,012 | A | | 11/1975 | Patel | |
| 4,482,112 | A | | 11/1984 | Cummings | |
| 4,488,715 | A | * | 12/1984 | Comeau | 5/647 |
| 4,524,768 | A | | 6/1985 | Serrao | |
| 4,662,366 | A | * | 5/1987 | Tari | 128/877 |
| 4,858,625 | A | * | 8/1989 | Cramer | 128/872 |
| 5,012,821 | A | | 5/1991 | Tarver | |
| 5,076,288 | A | | 12/1991 | Millard et al. | |
| 5,228,457 | A | * | 7/1993 | Kawamura | 5/607 |
| 5,546,963 | A | | 8/1996 | Doody | |
| 5,549,121 | A | | 8/1996 | Vinci | |
| 5,595,192 | A | | 1/1997 | Tatum | |
| 6,308,353 | B1 | | 10/2001 | Van Steenburg | |
| 6,928,674 | B2 | * | 8/2005 | Blackburn | 5/482 |
| 7,954,187 | B1 | * | 6/2011 | Earnest | 5/494 |
| 2005/0091749 | A1 | * | 5/2005 | Humbles | 5/646 |
| 2008/0053464 | A1 | | 3/2008 | Wilson | |
| 2010/0275377 | A1 | * | 11/2010 | West | 5/621 |

* cited by examiner

Primary Examiner — Robert G Santos
Assistant Examiner — Brittany Wilson
(74) Attorney, Agent, or Firm — Knobbe, Martens, Olson & Bear, LLP

(57) ABSTRACT

A soft arm support and protection device for use during a medical procedure when a patient is lying supine or prone. The device may be made from a soft neoprene material which is positioned under the patient's body. Enveloping leaves of material wrap from above and below the arm to afford complete and even support. The mating surfaces of the leaves are fitted with wide fastening material to allow secure fixation of the arm without pressure points. The dimensions allow for protected and stable vascular access sites with the option of adding additional foam padding about such sites and to vulnerable nerves and bones. The device also allows for radiologic imaging and can be quickly undone in an emergency for rapid access. The device is made of material which is hypoallergenic and durable. It can be manufactured in either a disposable or reusable version.

20 Claims, 7 Drawing Sheets

SOFT SURGICAL ARM SUPPORT

CROSS-REFERENCE TO RELATED APPLICATIONS

This application claims priority from U.S. Provisional Application No. 61/221,492, filed Jun. 29, 2009, which is hereby incorporated by reference in its entirety for all purposes.

BACKGROUND

1. Field of the Disclosure

The disclosure relates to devices for providing support and protection for a patient's arms during medical procedures.

2. Description of the Related Art

Often during medical procedures, for example surgery, a patient may be under a general anesthetic or sedated to such an extent that he or she cannot protect or support himself/herself, as well as voice or indicate pain or discomfort to those in care of him/her. In addition, the precision and accuracy of the outcome of the medical procedure may be greatly improved by maintaining the patient in a secure and motionless position. The medical staff is responsible for taking every precaution to protect the patient when he or she is most vulnerable and unable to protect himself/herself.

A number of devices have been developed to support and protect the arms of a patient in these circumstances. Rigid arm boards, on which the patient's arms are placed in various degrees of abduction from their body, often work quite well. However, when medical personnel need the arms positioned close to the body, these arm boards may prove too bulky and can often interfere with access to the patient for both the staff and equipment. In certain laparoscopic surgeries, including robotic assisted laparoscopic surgery, the patient's arms need to be snuggly adducted to their sides. Often a draw sheet is placed under the patient and the arms are tucked in to the patient's side. This maneuver can sometimes dislodge sites of vascular access or binding and create pressure points along the patient's arms, resulting in injury and damage to the nerves, which can be more problematic for the patient's recovery than the original surgery.

Arm sleds or toboggans (named for their resemblance to such items) have also been used with varying success. These are often made of rigid plastic or metal. The "C" shaped end of these devices cradles the arm and the extended portion passes under the mattress beneath the patient. These devices can be cumbersome to position since the mattress on a surgical table is usually secured in the middle from head to toe with a wide strip of VELCRO® brand hook-and-loop fasteners. Most often the sled has to be positioned with the mattress lifted up. If sleds are needed for both arms, the mechanics of the problem become compounded. In addition, these sleds are very rigid, can interfere with the access of the medical staff to the patient, and are not very forgiving of the soft tissue or bones of the patient. Additional padding is often required, and pressure points are common since the weight of the patient's arm is not evenly distributed. Finally these devices can interfere with radiographic imaging, especially the metal sleds.

A number of arm supports have been developed. Many rely on single or multiple straps or strap and buckle variations to secure the arms to the patient's side. In some models the patient ultimately rests on top of the strap which can press into the skin of the back. In other devices, releasing the device requires moving the patient from side to side. Certain devices support only the forearm. Existing devices may not evenly distribute or support the weight of the arm, which may create pressure points, which in turn may cause injuries.

Some devices, for example the device described in U.S. Pat. No. 3,861,666, cover part of the torso of the patient as well as the arms, which may interfere with medical procedures. Other devices, for example the device describe in U.S. Patent Pub. No. 2005/0091749, have protector sections that wrap over the arm from the outside of the arm and that are connected to a surface of the device. The attachment tape that connects the protector sections to the surface is positioned between the patient's arm and the patient's body, so it may be difficult to see the attachment tape to secure or release it, especially if the patient's body is resting on the attachment tape. Also, because the attachment tape connects to a protector section at only one point, an entire protector section must be either secured around the arm or not secured around the arm. Some other devices, for example the device describe in U.S. Patent Pub. 2008/0053464, have sleeves that hold the arms and have straps to secure the device in place. However, these straps may create pressure points, and the sleeves allow an entire arm to only be either covered or uncovered. Also, positioning the arm in the sleeve may require moving the patient's body.

SUMMARY OF THE DISCLOSURE

The devices of the invention each have several aspects, no single one of which is solely responsible for its desirable attributes. Without limiting the scope of the invention, certain features will now be discussed briefly.

In one embodiment, a patient restraint device comprises a body section dimensioned to receive a torso of a patient, wherein the body section includes first and second lateral edges, a first arm restraint attached to the first lateral edge, wherein the first arm restraint includes a first flexible member that is dimensioned to extend substantially continuously along a first length comprising a length of the patient's first arm from a location adjacent the patient's shoulder to a location adjacent the patient's wrist, and extend about a bottom surface and an outer periphery of the patient's first arm, and wherein the first arm restraint further includes a second flexible member dimensioned to extend substantially continuously along the first length, and extend about an inner periphery of the patient's first arm and mate with the first flexible member substantially continuously along the first length.

In one embodiment, a patient restraining device comprises a support surface dimensioned to receive a torso of a patient, a flexible inner panel dimensioned to extend about an inner periphery of a first arm of the patient, and a flexible outer panel dimensioned to extend about an outer periphery of the first arm to define a space with the flexible inner panel, wherein the space is dimensioned to receive the first arm.

In one embodiment, a method for securing an arm of a patient comprises resting a torso of a patient on a support surface, positioning a first flexible member over a surface of the patient's arm proximate to the torso along a first length, wherein the first length substantially extends from the patient's shoulder to the patient's wrist, and positioning a second flexible member over a surface of the patient's arm distal to the torso along the first length, thereby positioning the arm in a space defined by the first and second flexible members.

DETAILED DESCRIPTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
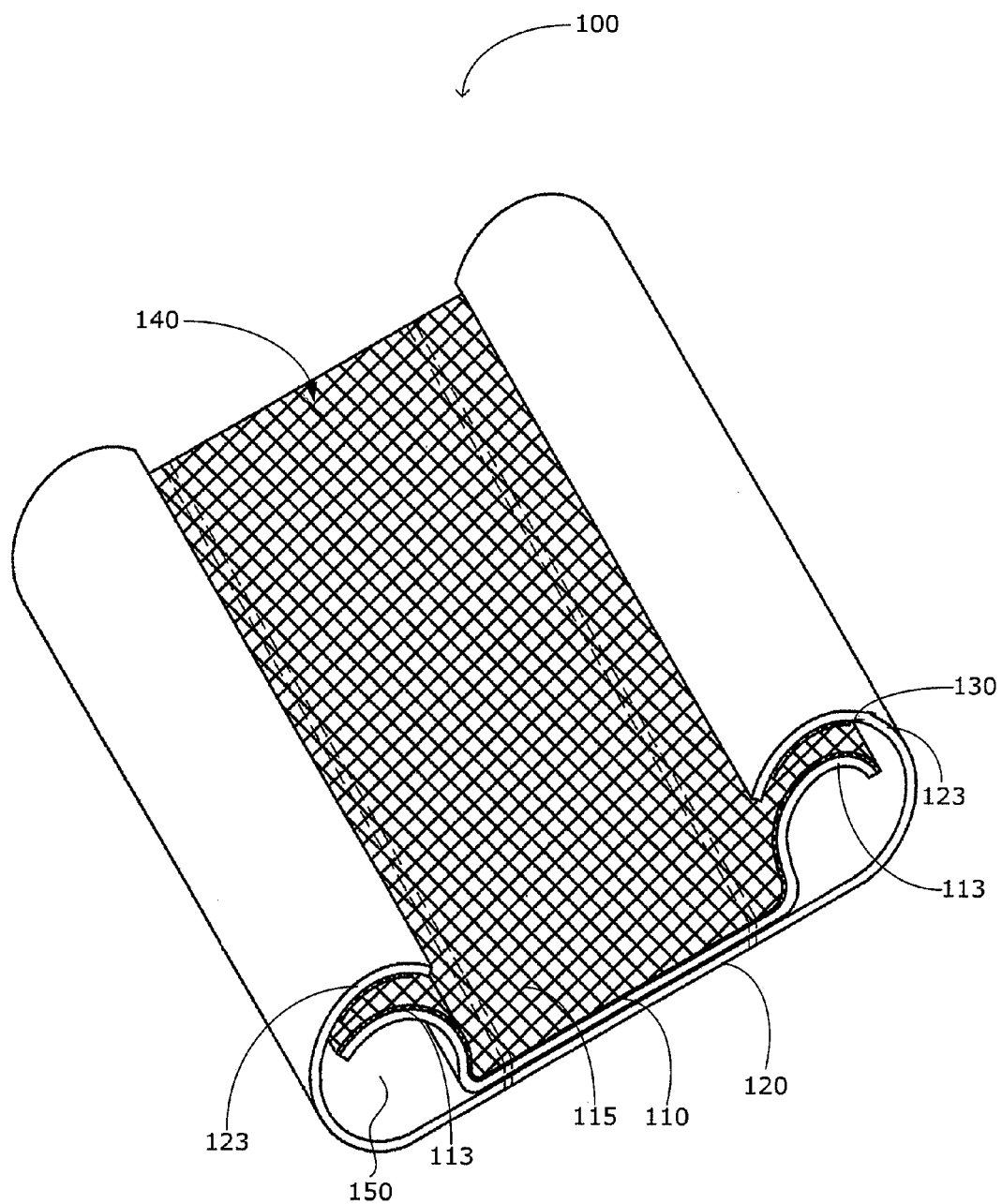
FIG. 1 is a perspective view of one embodiment of a soft surgical arm support.

FIG. 1 is a perspective view of one embodiment of a soft surgical arm support 100. In the embodiment shown in FIG. 1, the soft surgical arm support 100 includes a first panel 110 and a second panel 120. In one embodiment, the first panel 110 is made from 5 mm neoprene. Other embodiments may be made include other materials or material of different thicknesses, including other polymers (for example, synthetic rubbers, nylon, and polyester), synthetic fibers (for example, spandex), and/or natural fibers (for example, paper and cotton). Some materials may advantageously not interfere with radiologic imaging of the patent, may be hypoallergenic, and/or may be very durable. Depending on the embodiment, the soft surgical arm support 100 may be disposable or reusable. The other components of the soft surgical arm support 100 may be made from the same materials that the first panel 110 may be made from.

The first panel 110 is proximate to the patient and includes a support surface 115. The first panel 110 may be completely or partially covered by a fleece material 140. The fleece material 140 may provide extra cushioning for a patient and may provide a surface that is more comfortable to a patient's skin. The fleece material 140 may act as a fastener, for example the loop surface of a hook-and-loop fastener. The first panel 110 includes one or more first flexible members 113. A first flexible member 113 may include a portion of the first panel 110 adjacent to an edge of the first panel 110 that may move independently of the second panel 120. In one embodiment, one or more of the first flexible members 113 extend substantially the entire length of an edge of the first panel 110. The fleece material 140 may cover all or part of the first flexible member 113.

The second panel 120 includes one or more second flexible members 123. A second flexible member 123 may include a portion of the second panel 120 near an edge of the second panel 120 that moves independently of the first panel 110. A second flexible member 123 may extend substantially the entire length of an edge of the second panel 120 and includes a fastener, for example a fastening surface 130. The fastening surface 130 may extend substantially the entire length of the second flexible member 123. The first flexible member 113 and the second flexible member 123 may be dimensioned to continuously extend along a length substantially equal to a distance between a patient's wrist and shoulder.

The first flexible member 113 may be coupled to the second flexible member 123, thereby defining a space 150. The space 150 may be dimensioned to receive an arm of a patient, and, for example, may substantially be in the shape of an open-ended cylinder. For example, the first flexible member 113 is bent in an arc to form a first part of a circumference of the space 150 and the second flexible member 123 is bent in an arc to form a second part of the circumference of the space 150. The second flexible member 123 overlaps the first flexible member 113, and the first flexible member 113 is coupled to the second flexible member 123 at the overlap, for example using the fastening surface 130 and the fleece 140. Alternatively, the first flexible member 113 may overlap the second flexible member 123. Also, some embodiments may omit the first flexible member 113 or the second flexible member 123, and the remaining flexible member may wrap over the arm to be coupled to the support surface 150.

In one embodiment, the first flexible member 113 includes a loop surface, such as the fleece material 140, and the second flexible member 123 includes a hook surface 130, though the positions of the hook and/or loop surfaces may be switched. The fasteners on both the first flexible member 113 and the second flexible member 123 may be on the side proximal to the patient or distal to the patient, thereby creating a standing seam that extends away from or a seam that extends toward the patient's arm when the first flexible member is coupled to the second flexible member 123. Also, in other embodiments the first flexible member 113 does not overlap the second flexible member 123 or other fasteners are used, including adhesives (e.g., temporary adhesives), buttons, zippers, and laces.

The second flexible member 123 and/or the first flexible member 113, as well as the space 150, may be substantially the same length as a patient's arm. This advantageously provides support or protection for substantially the entire arm. For example, the soft surgical arm support 100 may provide an extra layer of protection against cuts, scrapes, punctures, burns, etc., caused by undesired contact with surgical instruments, chemicals, etc. Also, in embodiments in which the fastening surfaces (for example, the fastening surface 130 and the fleece material 140) extend substantially the entire length of the second flexible member 123 and the first flexible member 113, the second flexible member 123 may be coupled to the first flexible member 113 along substantially the entire length of the arm. This may distribute the force holding the arm in place along substantially the entire length of the arm, thereby reducing or eliminating pressure points on the arm. This advantageously reduces the risk of injury to a patient from pressure points, especially a patient who is sedated or unconscious.

In use, the soft surgical arm support 100 is positioned on a patient bed. Since the soft surgical arm support 100 may be placed on top, there is no need to lift the bed or mattress to position the soft surgical arm support 100. A patient is positioned by lying down on the support surface 115. The first flexible member 113 is positioned around the inner periphery of the arm. The second flexible member 123 is positioned around the outer periphery of the arm, thereby positioning the arm in the space 150. The second flexible member 123 is coupled to the first flexible member 113 to secure the first flexible member 113 to the second flexible member 123, thereby securing the arm in place. It will be appreciated that positioning the first flexible member 113 and the second flexible member 123 may require little or no movement of the patient. The patient's arm may need to be lifted, but the patient's body does not need to be lifted from the support surface 115 to position the arm in the space. This reduces the risk of injury to the patient, who may be unconscious, heavily sedated, or otherwise unable to voluntarily move, and to medical personnel who would otherwise need to lift the patient. It also reduces the need to have multiple medical personnel lift and move the patient or the need to use equipment, for example a lift, to move the patient. It increases the speed of securing the arm of the patient and further allows the arm to be quickly released to provide rapid access to the arm in an emergency.

Moreover, in some embodiments the second flexible member 123 and the first flexible member 113 extend to an upper surface of the circumference of the arm, which advantageously positions the interface between the second flexible member 123 and the first flexible member 113 on top of the arm, increasing the visibility of the interface between the second flexible member 123 and the first flexible member 113. This further facilitates uncoupling the second flexible member 123 from the first flexible member 113 because the arm and the patient do not need to be moved to uncouple the members and because medical personnel can easily see where to grasp the second flexible member 123 and the first flexible member 113 to uncouple them. This improves access to the arm of the patient, for example to attach a medical device to the arm (such as an IV, a sensor, a bandage, etc.), to perform a medical procedure on the arm, or to release the arm.

It will also be appreciated that in some embodiments the first flexible member 113 may be selectively decoupled from the second flexible member 123 along a portion of the interface between the members. This may allow medical personnel to access a portion of the arm while permitting the arm to be supported and protected by the first flexible member 113 and the second flexible member 123. For example, medical personnel may decouple the first flexible member 113 from the second flexible member 123 adjacent to the forearm to attach an IV to the patient while leaving the first flexible member 113 coupled to the second flexible member 123 along the rest of the length of the arm (including the upper arm and wrist, for example), thereby holding the arm in place and protecting the enclosed portion of the arm while the IV is attached. Medical personal may adjust the location where they decouple the first flexible member 113 and the second flexible member 123 to access the arm in order to account for differences in arm lengths. Furthermore, some fasteners, for example hook-and-loop fasteners, may be coupled around a medical device (for example, a tube or a wire), which allows the arm to be re-enclosed in the space 150 while leaving the medical device attached to the arm and providing additional support to hold the medical device in a desired position.

Figure 2A:
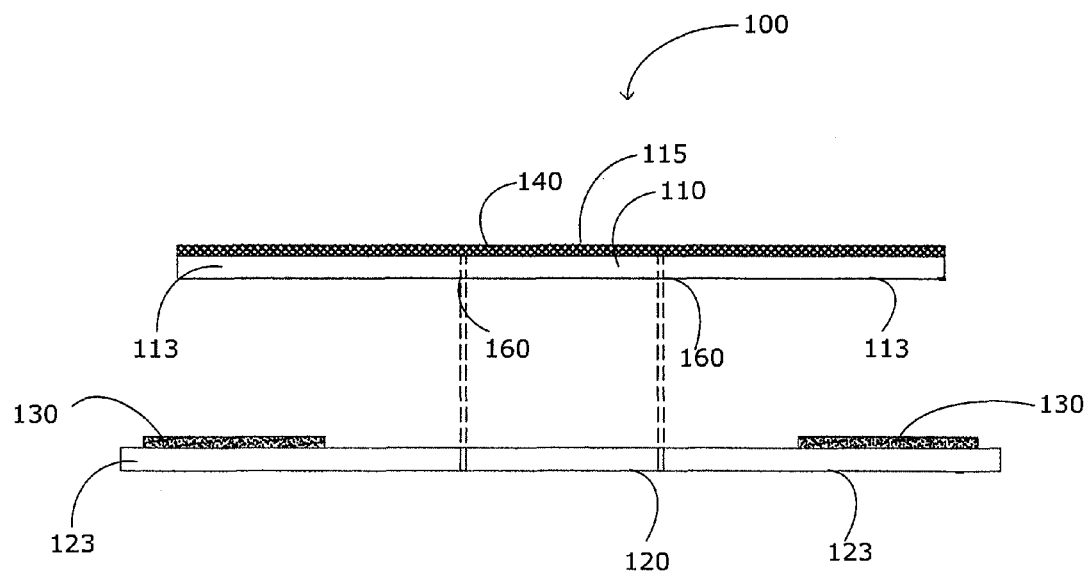
FIG. 2A is an exploded side view of one embodiment of a soft surgical arm support.

FIG. 2A is an exploded side view of one embodiment of a soft surgical arm support. In FIG. 2A, the first flexible members 113 and the second flexible members 123 are in a substantially planar position. The first panel 110 is coupled to the second panel 120 at one or more fastening points 160, for example by stitching, fasteners, or adhesive. Alternatively, the first panel 110 may be coupled to the second panel 120 along a larger or a smaller surface than is shown by FIG. 2A, for example along part of or the entire surface between the fastening points 160.

Figure 2B:
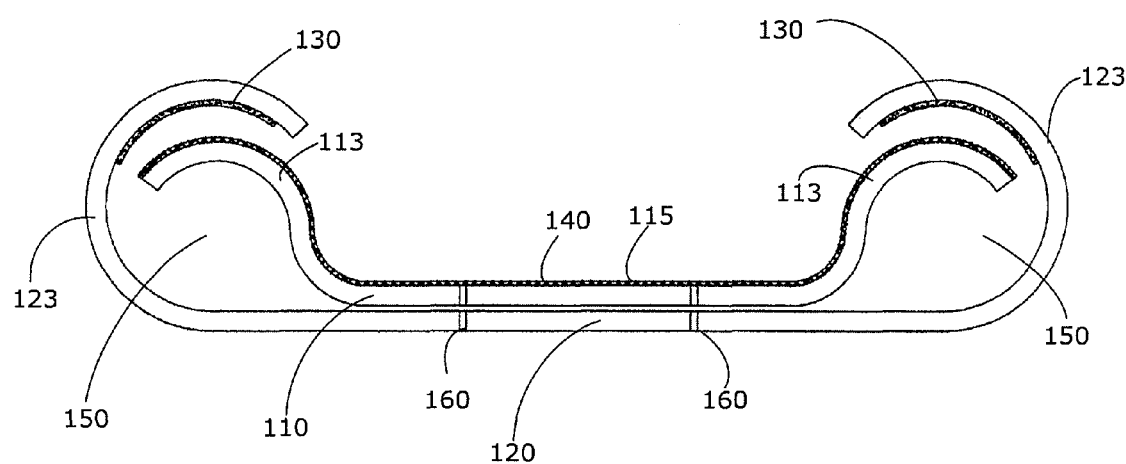
FIG. 2B is a side view of one embodiment of a soft surgical arm support.

FIG. 2B is a side view of one embodiment of a soft surgical arm support. In FIG. 2B, the first flexible members 113 and the second flexible members 123 are positioned to form the spaces 150 that receive the arms of a patient. Though the second flexible members 123 are shown as being coupled to and extending around part of the outer periphery of the first flexible members 113, in other embodiments the first flexible members 113 may be coupled to and extend around part of the outer periphery of the second flexible members 123. Some embodiments may allow the first flexible member 113 and the second flexible member 123 to be coupled in either position. Also, some embodiments may allow the first flexible member 113 to be coupled to the second flexible member 123 in a standing seam or may allow for different coupling positions along the length of the interface, for example a position where the first flexible member 113 overlaps the second flexible member 123 along one portion of the arm and where the second flexible member 123 overlaps the first flexible member 113 along another portion of the arm.

The dimensions of the fastening surface 130, the fleece material 140, the first flexible member 113, and/or the second flexible member 123 allow the first flexible member 113 and the second flexible member 123 to be coupled together at a range of positions. This range allows medical personnel to selectively vary the size of the space 150 along the entire length of the arm, which allows the fit to be adjusted according to a size of a patient's arm and/or a desired snugness around the arm. It also allows the space 150 to accommodate padding placed around the arm. For example, in some embodiments if a larger space 150 is desired, the first flexible member 113 may be coupled to the second flexible member 123 in a position when there is minimal overlap of the fastening surfaces. If a smaller space is desired, the first flexible member 113 may be coupled to the second flexible member 123 in a position where there is more overlap. Also, the range of positions may allow the size of the space 150 to vary along all or part of the length of the arm (for example, the space may be wider near the bicep and narrower near the wrist) so that the arm is snugly enclosed along the entire length of the arm. This advantageously reduces pressure points on the arm by more evenly distributing the pressure along the entire length of the arm. In the embodiment shown in FIGS. 2A-2B, the dimensions of the fleece allow the range of overlaps to extend from minimal overlap to an overlap greater than the width of the surface of the first flexible panel 113.

Figure 3A:
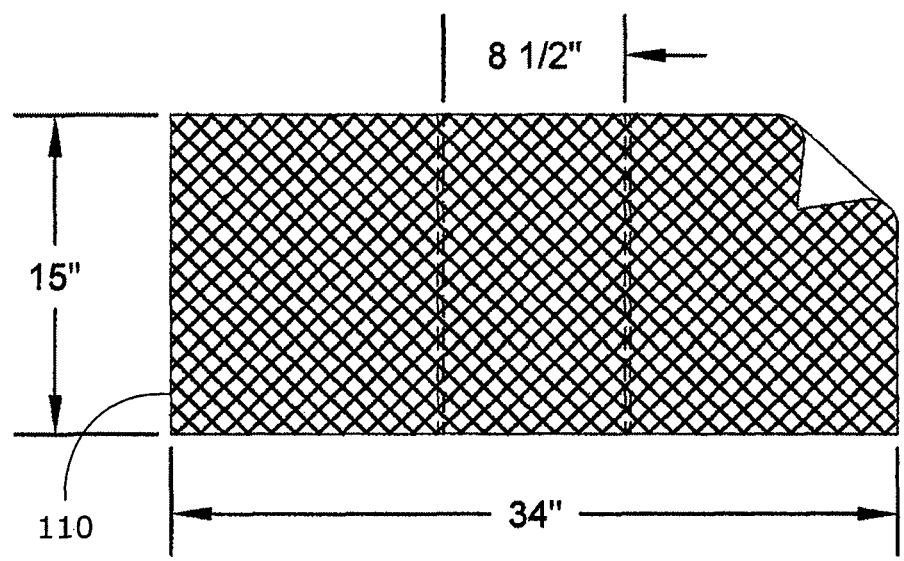
FIG. 3A is a top down view of one embodiment of a first panel of a soft surgical arm support.
Figure 3B:
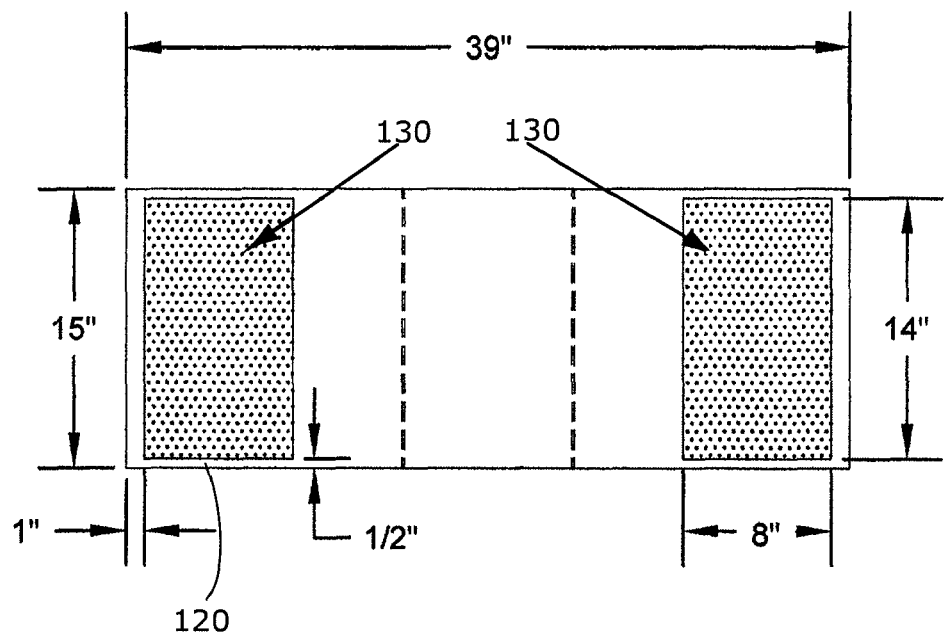
FIG. 3B is a top down view of one embodiment of a second panel of a soft surgical arm support.

FIG. 3A is a top down view of one embodiment of a first panel 110 of a soft surgical arm support, and FIG. 3B is a top down view of one embodiment of a second panel 120 of a soft surgical arm support. Though these figures illustrate the dimensions of one embodiment, it is to be understood that all dimensions are provided by way of example rather than limitation, and any other suitable dimensions in addition to and/or in alternative to the illustrative dimensions of the described embodiment may be used in other embodiments. The first panel 110 measures about 34 inches long and about 15 inches wide. The second panel 120 measures about 39 inches long and about 15 inches wide. One panel is about 5 mm thick and the other panel is about 3 mm thick. Each end of the second panel includes an approximately 8 inch long by 14 inch wide piece of a fastening surface 130. In this embodiment, the fastening surface 130 is offset from the lateral edge by about 1 inch and from the top and bottom edges by about ½ inch. The second panel 120 is coupled to the first panel 110, for example by sewing, at a point about 15 inches from each lateral edge. In other embodiments, the panels may be attached to each other with any other suitable fastener, for example buttons, zippers, adhesives, hook and loop fasteners, and/or laces.

The soft surgical arm support 100 may be placed on a table so that the lower edge of the soft surgical arm support 100 is positioned approximately at the level of the wrist when at the patient's side and the soft surgical arm support 100 is centered on the table from side to side. The second flexible members 123 may be allowed to hang over the edges of the table as the patient is moved into position. The patient is positioned on the table and on the soft surgical arm support 100. IV access on the patient can be placed and secured. Additional padding may be used, for example around vulnerable sites such as IV sites, soft tissue, nerves, and bones. The patient's arms and any additional padding are placed between the second flexible members 123 and the first flexible members 113. The second flexible members 123 wrap around the outside of the arm and the first flexible members 113 wrap around the inside of the arm. The device may encase all or part of the arm and provide even and uniform support from the wrist to just above the elbow or substantially to the shoulder.

Figure 4:
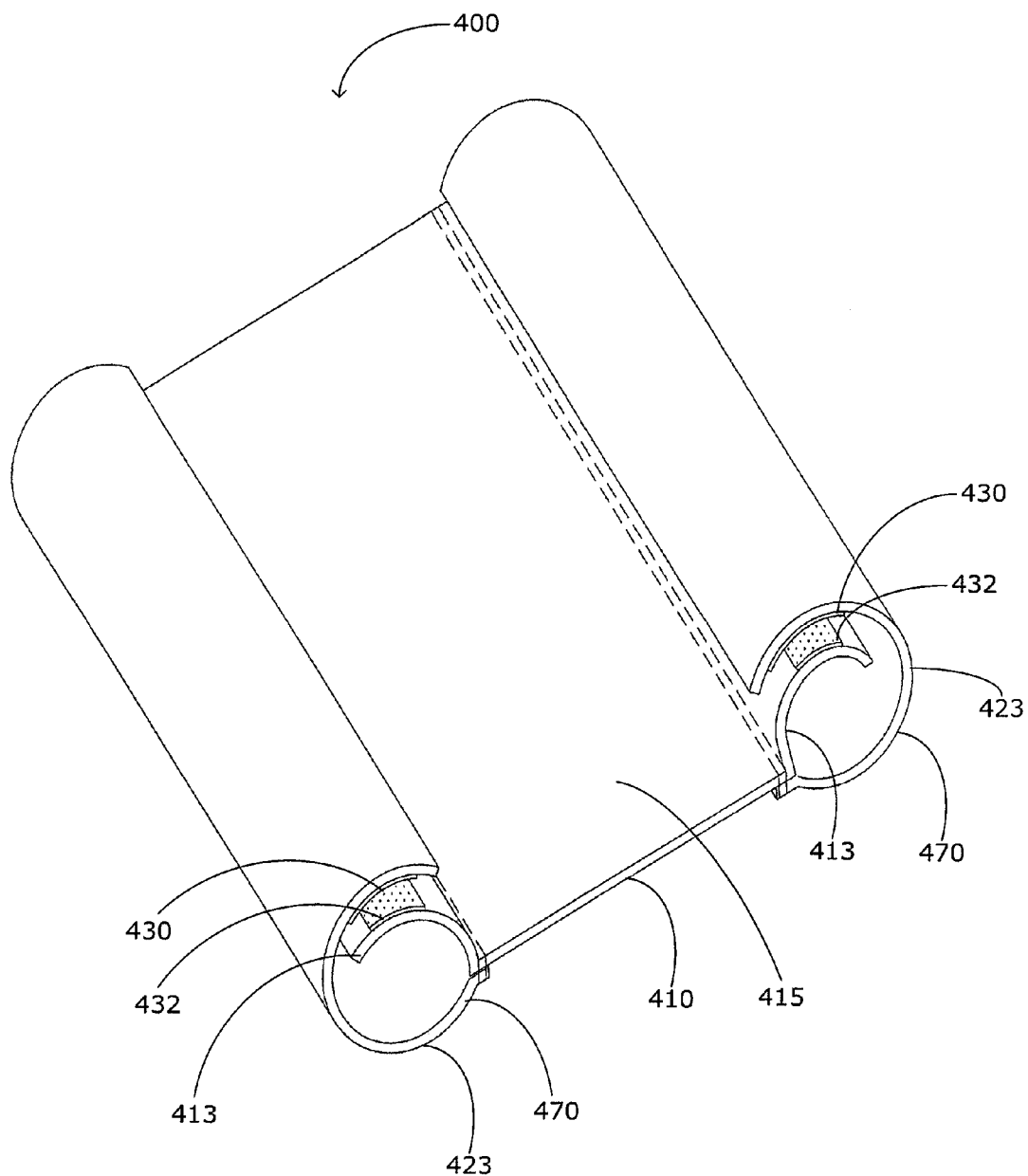
FIG. 4 is a perspective view of one embodiment of a soft surgical arm support.

FIG. 4 is a perspective view of one embodiment of a soft surgical arm support 400. In the embodiment shown in FIG. 4, the device includes a first panel 410 and two additional panels 470. It will be appreciated that in other embodiments the soft surgical arm support 400 may include another numbers of panels. The first panel 410 is proximate to the patient and includes a support surface 415, though in other embodiments one or both of the additional panels 470 may be proximate to the patient. The first panel 410 includes one or more first flexible members 413. The first flexible members 413 each include a fastening surface 432. The additional panels 470 are coupled to a distal surface of the first panel 410. The additional panels 470 include a fastening surface 430 that may engage the fastening surface 432 of the first flexible members 413.

Figure 5A:
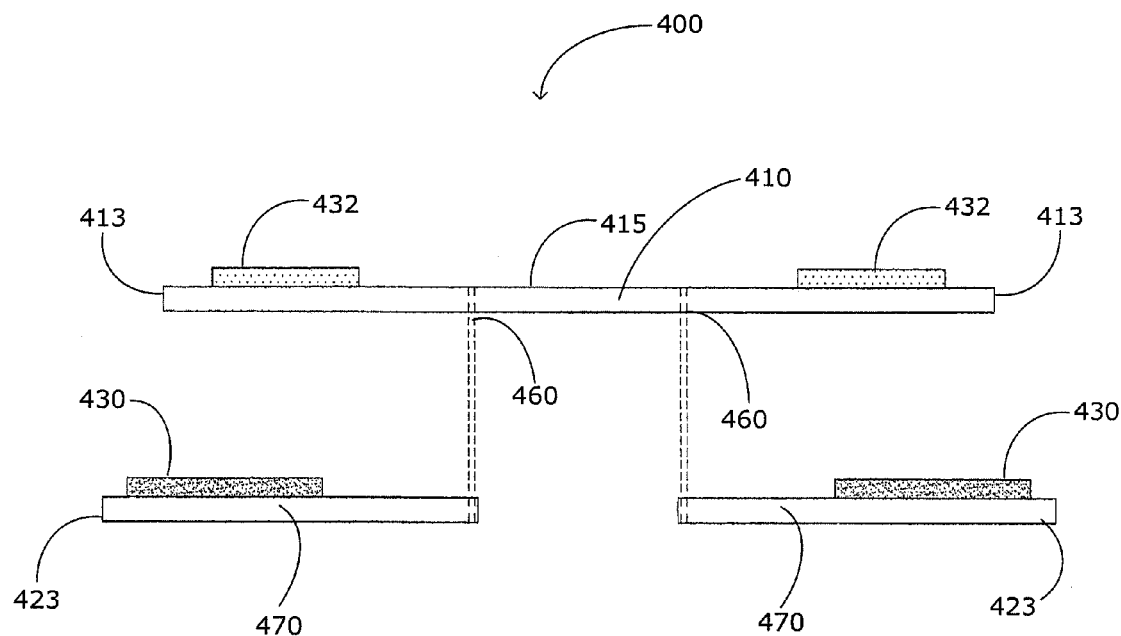
FIG. 5A is an exploded side view of one embodiment of a soft surgical arm support.
Figure 5B:
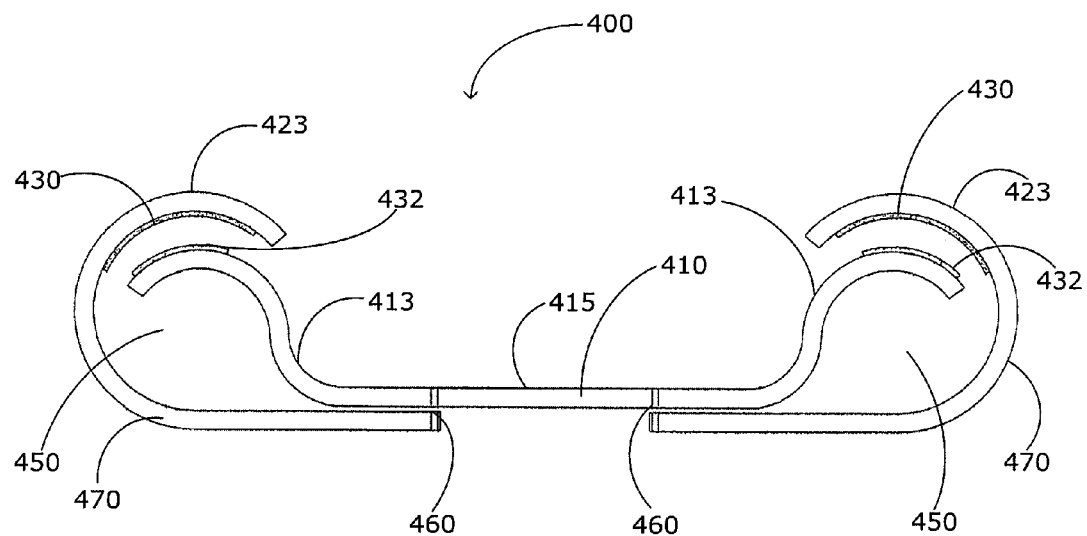
FIG. 5B is a side view of one embodiment of a soft surgical arm support.

FIG. 5A is an exploded side view of one embodiment of a soft surgical arm support 400, and FIG. 5B is a side view of one embodiment of the soft surgical arm support 400. The additional panels 470 are coupled to the first panel 410 at the fastening points 460. As shown in FIG. 5B, a first flexible member 413 may be bent or curved into a substantially arc shape and an additional panel 470 may be bent or curved into a substantially arc shape that contacts the first flexible member 413 in order to define a space 450 dimensioned to receive an arm of a patient. It will be appreciated that the first flexible member 413 and the additional panel 470 may overlap, and the dimensions of the fastening surfaces 430, 432 may allow the extent of the overlap to vary, thus allowing the size of the space 450 to vary.

Figure 6A:
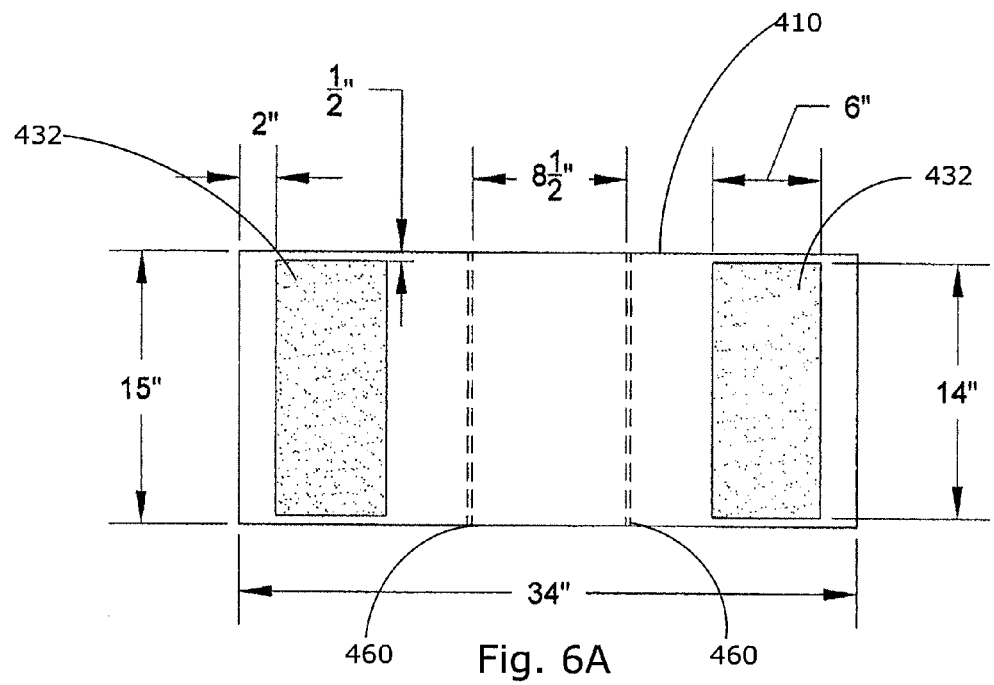
FIG. 6A is a top down view of one embodiment of a first panel of a soft surgical arm support.
Figure 6B:
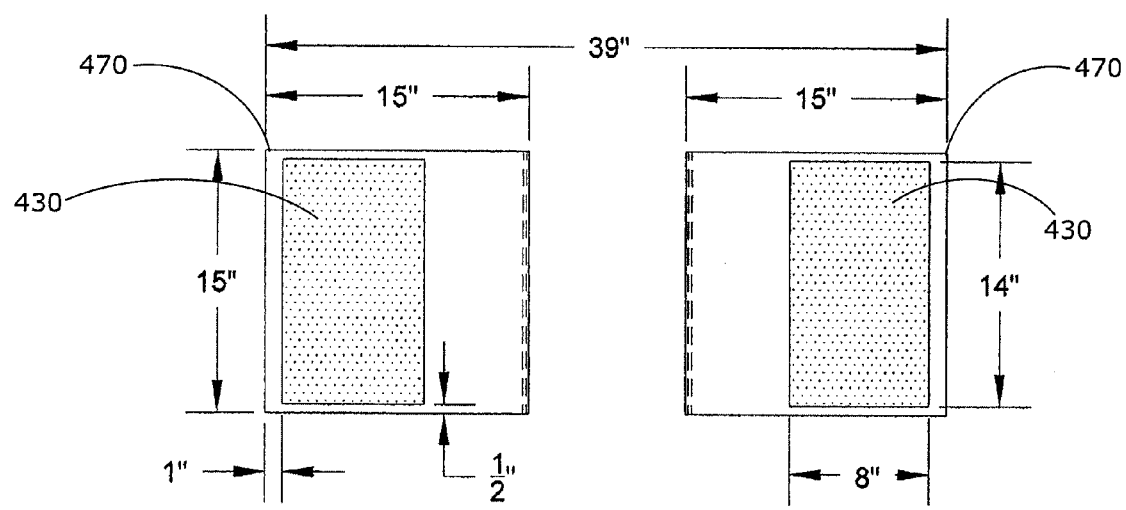
FIG. 6B is a top down view of one embodiment of additional panels of a soft surgical arm support.

FIG. 6A is a top down view of one embodiment of a first panel 410 of a soft surgical arm support 400, and FIG. 6B is a top down view of one embodiment of the additional panels 470 of a soft surgical arm support 400. Again, though these figures illustrate the dimensions of one embodiment, it is to be understood that all dimensions are provided by way of example rather than limitation, and any other suitable dimensions in addition to and/or in alternative to the illustrative dimensions of the described embodiment may be used in other embodiments. The first panel 410 is about 34 inches long and about 15 inches wide. Each end of the first panel 410 includes an approximately 6 inch long and 14 inch wide piece of a fastening surface 432. The fastening surface 432 is offset from the lateral edges of the first panel 410 by 2 inches and from the top and bottom edges of the first panel 410 by ½ inch.

The additional panels 470 each are about 15 inches long and about 15 inches wide. Each additional panel 470 has an approximately 8 inch long by 14 inch wide piece of a fastening surface 430. The fastening surface 420 is offset from the lateral edge of the additional panel 470 by about 1 inch and from the top and bottom edges of the additional panel 470 by about ½ inch. The additional panels 470 are coupled to the first panel 410, one at each fastening point 460, which are about 11 inches from the lateral edge of the first panel 410. The fastening surfaces 430 of the additional panels 470 are oriented in the same direction. The dimensions of the fastening surface 420 and the fastening surface 430 in this allow an overlap range of approximately 14 inches when the additional panel 470 is coupled to an end of the first panel 410, though other embodiments may have different ranges. This range may be used to adjust the snugness or tightness of a fit around a patient's arm.

Figure 7A:
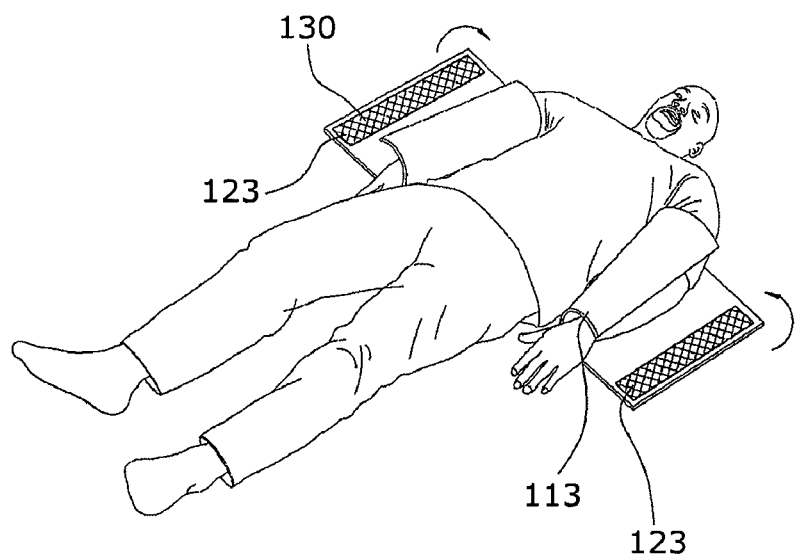
FIG. 7A is a perspective view of one embodiment of a soft surgical arm support in use with a patient.

FIG. 7A is a perspective view of one embodiment of a soft surgical arm support in use with a patient. In FIG. 7A, the first flexible members 113 are positioned around the inner circumference of the respective arms of the patient. In the embodiment shown, the second flexible members 123 are extending outward. The first flexible members 113 and the second flexible members extend substantially from the patient's wrists to the patient's shoulders.

Figure 7B:
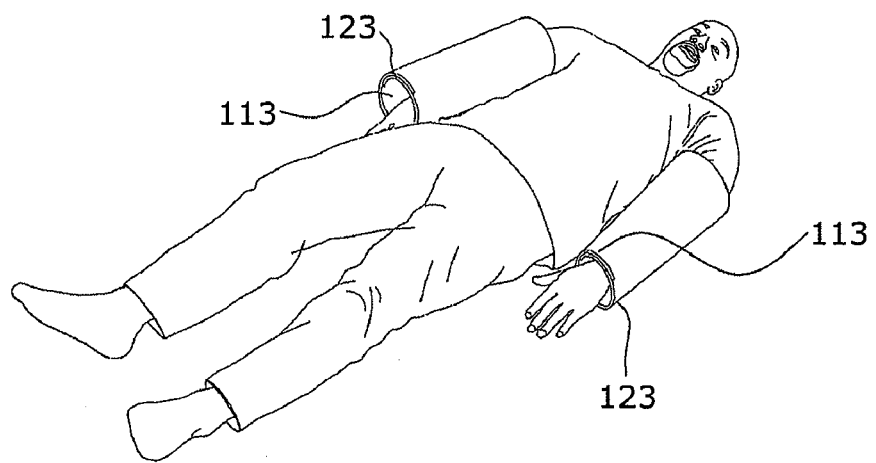
FIG. 7B is a perspective view of one embodiment of a soft surgical arm support in use with a patient.

FIG. 7B is a perspective view of one embodiment of a soft surgical arm support in use with a patient. In FIG. 7B, the second flexible members 123 have been folded over the outside of the first flexible members 113 and the arms of the patient. The arms of the patient are substantially enclosed by the first flexible members 113 and the second flexible members 123. Because the first flexible members 113 and the second flexible members 123 are coupled together on the upper peripheries of the patient's arms, the body and arms of the patient do not need to be moved when the flexible members 113, 123 are coupled together. Also, substantially the entire arm is enclosed, providing protection for the arm. Furthermore, because the flexible members 113 and 123 are coupled along substantially the entire length of the arm, the pressure on the arm is more evenly distributed along the length of the arm, thereby reducing pressure points. Moreover, the fit around the arm may be selectively adjusted along substantially the entire length of the arm (e.g., wider at the bicep and forearm, narrower at elbow and wrist) so that the fit is snug along the length.

Although the foregoing invention has been described in terms of certain embodiments, other embodiments will be apparent to those of ordinary skill in the art from the disclosure herein. Moreover, the described embodiments have been presented by way of example only, and are not intended to limit the scope of the inventions. Indeed, the novel devices described herein may be embodied in a variety of other forms without departing from the spirit thereof. Accordingly, other combinations, omissions, substitutions and modifications will be apparent to the skilled artisan in view of the disclosure herein. Thus, the present invention is not limited by the preferred embodiments, but is defined by the appended claims.

What is claimed is:

1. A patient restraint device comprising:
   a body section dimensioned to receive a torso of a patient, wherein the body section includes first and second lateral edges and has a first and a second surface, wherein the first surface receives the patient and the second surface is adapted to be positioned on an exterior surface;
   a first arm restraint attached to the first lateral edge, wherein the first arm restraint includes a first flexible member that is dimensioned to extend substantially continuously along a first length comprising a length of the patient's first arm from a location above the patient's elbow to a location adjacent the patient's wrist, and extend outward from the first lateral side about a bottom surface adjacent the exterior surface and then about an outer periphery of the patient's first arm away from the exterior surface; and wherein the first arm restraint further includes a second flexible member dimensioned to extend substantially continuously along the first length, and extend outward from the first lateral edge adjacent the first side and upwards away from the first surface of the body section about an inner periphery of the patient's first arm and mate with the first flexible member at a point adjacent an upper surface of the patient's arm located away from the exterior surface substantially continuously along the first length so as to be secured thereto substantially along the first length and so that the engagement between the first and second flexible member urges the patient's arm inward towards the patient's torso positioned on the first surface of the body section.

2. The device of claim 1, further comprising:

a second arm restraint attached to the second lateral edge, wherein the second arm restraint comprises a third flexible member that is dimensioned to extend substantially continuously along a second length comprising a length of the patient's second arm from a location adjacent the patient's shoulder to a location adjacent the patient's wrist, and extend about a bottom surface and an outer periphery of the patient's second arm, thereby receiving the second arm in a first space that substantially extends the second length, and wherein the second arm restrain comprises a fourth flexible member dimensioned to extend substantially continuously along the second length and extend about an inner periphery of the patient's second arm and mate with the third flexible member substantially continuously along the second length.

3. The device of claim 1, wherein the first and second flexible members comprise a neoprene material.

4. The device of claim 3, wherein the first and second flexible members comprise hook-and-loop fasteners that substantially extend the first length.

5. The device of claim 3, wherein the neoprene material is about 5 mm thick.

6. The device of claim 1, wherein the body is about 39 inches long and about 15 inches wide.

7. The device of claim 1, wherein the first flexible member is about 15 inches long and about 15 inches wide.

8. The device of claim 1, wherein a surface of the body section comprises a fleece material.

9. A patient restraining device comprising:

a support surface dimensioned to receive a torso of a patient having a first side that receives the patient and a second side that is positioned on an exterior surface;

a flexible inner panel dimensioned to extend about an inner periphery of a first arm of the patient from the first side of the support surface; and a flexible outer panel dimensioned to extend about an outer periphery of the first arm adjacent the exterior surface underneath the patient's arm to define a space with the flexible inner panel, wherein the space is dimensioned to receive the first arm wherein the flexible inner panel and the flexible outer panel are dimensioned so as to be secured to each other at a location adjacent an upper surface of the patient's arm located away from the exterior surface substantially continuously along the length of the patient's arm from above their elbow to their wrist so that the engagement between the flexible inner panel and the flexible outer panel urges the patient's arm inward towards the patient's torso positioned on the support surface.

10. The device of claim 9, wherein the flexible outer panel and the flexible inner panel are coupleable along a first length.

11. The device of claim 10, wherein the first length is substantially equal to a distance between a wrist and a shoulder of the patient.

12. The device of claim 11, wherein the flexible outer panel and the flexible inner panel are selectively decoupleable along a portion of the first length.

13. The device of claim 10, wherein the flexible outer panel is dimensioned to overlap the flexible inner panel when the flexible outer panel is coupled to the flexible inner panel.

14. The device of claim 13, wherein the flexible outer panel allows a width of the overlap to selectively vary along the first length, thereby allowing adjustment of a size of the space to accommodate different arm thicknesses.

15. The device of claim 14, wherein the width of the overlap may selectively vary over a range of 14 inches.

16. The device of claim 10, wherein the flexible inner panel is dimensioned to overlap the flexible outer panel when the flexible outer panel is coupled to the flexible inner panel.

17. A method for securing an arm of a patient, comprising:

resting a torso of a patient on a first side of a support surface when a second side of the support surface is positioned on a receiving surface;

positioning a first flexible member over a surface of the patient's arm proximate to the torso along a first length, wherein the first length substantially extends from above the patient's elbow to the patient's wrist and wherein the first flexible member extends upward from the first side of the support surface away from the receiving surface;

positioning a second flexible member over a surface of the patient's arm distal to the torso along the first length, thereby positioning the arm in a space defined by the first and second flexible members wherein the second flexible member extends outward underneath the patient's arm so as to be adjacent the receiving surface; and coupling the first flexible member to the second flexible member long substantially the entire first length wherein the first flexible member is secured to the second flexible member at a location adjacent an upper surface of the patient's arm located away from the receiving surface so that the engagement between the first and second flexible panel urges the patient's arm inward toward the patient's torso positioned on the support surface.

18. The method of claim 17, further comprising positioning the second flexible member to overlap the first flexible member proximate to an upper surface of the arm.

19. The method of claim 17, further comprising coupling the first flexible member to the second flexible member along substantially the entire first length.

20. The method of claim 19, wherein the first flexible member is coupled to the second flexible member using hook-and-loop fasteners.

* * * * *